US00PP16034P3

(12) United States Plant Patent
Bradford

(10) Patent No.: US PP16,034 P3
(45) Date of Patent: Oct. 11, 2005

(54) NECTARINE TREE NAMED 'SPRING PEARL'

(50) Latin Name: *Prunus persica*
Varietal Denomination: Spring Pearl

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 91 days.

(21) Appl. No.: 10/738,340

(22) Filed: Dec. 18, 2003

(65) Prior Publication Data

US 2005/0138700 P1 Jun. 23, 2005

(51) Int. Cl.[7] ..... A01H 5/00
(52) U.S. Cl. ..... Plt./188
(58) Field of Search ..... Plt./188

(56) References Cited

U.S. PATENT DOCUMENTS

PP9,360 P * 11/1995 Bradford et al. ..... Plt./188
PP9,542 P * 5/1996 Zaiger et al. ..... Plt./188
PP14,248 P2 * 10/2003 Bradford ..... Plt./188
PP14,517 P2 * 2/2004 Slaughter et al. ..... Plt./188

OTHER PUBLICATIONS http://www.bradfordgenetics.com/june15–04.htm.*
http://www.bradfordgenetics.com/the_pearls.htm.*
http://www.bradfordgenetics.com/17P1203.htm.*

* cited by examiner

*Primary Examiner*—Anne Marie Grunberg
*Assistant Examiner*—W. C. Haas

(57) ABSTRACT

The present invention relates to a nectarine tree and more particularly to a new and distinct variety broadly characterized by a medium size, vigorous, hardy, self-fertile, productive and regular bearing tree. The fruit matures under the ecological conditions described approximately the third week in June, with first picking on Jun. 21, 2003. The fruit is uniformly large in size, excellent in flavor, globose in shape, clingstone in type, very firm in texture, white in flesh color, and red in skin color. The variety was developed as an open pollinated seedling from an unnamed white flesh nectarine.

1 Drawing Sheet

Botanical classification: *Prunus persica.*
Variety denomination: 'Spring Pearl'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'Spring Pearl'. During the spring and summer of 1997 I gathered fruit from several different unnamed seedlings in my experimental orchard located near Le Grand, Calif., in Merced County (San Joaquin Valley). One particular group of nectarines were white in flesh color, clingstone in type, and sub-acidic in flavor, and were thus designated as "WNC (OP)". The seeds from these fruits were removed, cracked, stratified, germinated and grown as seedlings on their own root in my greenhouse, and upon reaching dormancy transplanted to a cultivated area in the experimental orchard described above. During the fruit evaluation season of 2000 I selected several nectarines that exhibited desirable qualities, as the present variety was selected as a single tree from the group of "WNC (OP)" described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' rootstock (unpatented) upon which the present variety was compatible and true to type.

The present variety is most similar to 'June Pearl' (U.S. Plant Pat. No. 9,360) nectarine, by producing nectarines that are very firm in texture, sub-acidic and sweet in flavor, clingstone in type, and nearly full red in skin color, but is distinguished therefrom by producing fruit that is more globose in shape, has virtually no protruding tips at the apex, is larger in size, and matures about five days later.

SUMMARY OF VARIETY

In summary, the present variety is characterized by a medium size, vigorous, hardy, self-fertile, productive and regular bearing tree. The fruit matures under the ecological conditions described approximately the third week in June, with first picking on Jun. 21, 2003. The fruit is uniformly large in size, excellent in flavor, globose in shape, clingstone in type, very firm in texture, white in flesh color, and red in skin color. The variety was developed as an open pollinated seedling from an unnamed white flesh nectarine.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jun. 25, 2003, on the original tree grown on its own roots during its sixth growing season. All major color code designations are by reference to the Inter-Society Color Council, National Bureau of Standards. Common color names are also used occasionally.

TREE

Size: Medium, reaching a height of 11' [3.35 m.] and a spread of 10' [3.05 m.] after six growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Trunk:

*Size.*—Medium, with a maximum diameter of 3¾" [95 mm.] after the sixth growing season.

*Texture.*—Somewhat shaggy.

*Bark color.*—A two-tone variegation of Dark grayish yellowish brown [81. d.gy.yBr] and Dark brown [59. d.Br].

*Lenticels.*—Approximate number per square inch: 10. Color: Brownish orange [54. brO]. Typical Size: ⅛" to 7⁄16" [3.2–11.1 mm.]. Shape: Elliptical.

Branches:

*Size.*—Diameter of limb is 1½" [38 mm.] measured 12" above the secondary fork, typical of *Prunus persica*, and dependent upon cultural practices and climatic conditions.

*Texture.*—Smooth on 1st year wood, increasing roughness with age.

*Color.*—1st year wood topside: Moderate red [15. m.R]. 1st year wood underside: Brilliant yellow green [116. brill.YG]. Older wood: Deep yellowish brown [75. deep yBR].

*Lenticels.*—Approximate number per square inch: 100. Color: Moderate orange [53. m.O]. Typical size: 1⁄32" to ⅛" [0.8–3.2 mm.]. Shape: Elliptical.

Leaves:

*Size.*—Medium. Average length: 5⅝" [143 mm.]. Average width: 1½" [38 mm.].

*Arrangement.*—Alternate.

*Thickness.*—Medium.

*Form.*—Elliptical.

*Apex.*—Acuminate.

*Base.*—Acute, with an average base angle of 80 degrees.

*Surface.*—Smooth.

*Color.*—Dorsal surface: Moderate olive green [125. m.OlG]. Ventral surface: Moderate yellow green [120. m.YG].

*Margin.*—Finely serrate.

*Venation.*—Pinnately net veined.

*Petiole.*—Average length: ½" [12.7 mm.]. Average thickness: 1⁄16" [1.6 mm.]. Color: Brilliant yellow green [116. brill.YG].

*Stipules.*—Number: 2 per leaf, up to 6 per growing tip. Average length: 7⁄16" [11.1 mm.].

*Color.*—Strong yellow green [117. s.YG] when young, becoming light reddish brown [42. l.rBr] with age.

*Glands.*—Average number: 4. Position: Mostly alternate, first two on petiole, rest on base of blade. Size: Medium. Form: Reniform. Color: Brilliant yellow green [116. brill.YG] when young, acquiring a Moderate reddish orange [37. m.rO] center with age.

*Leaf buds.*—Conic.

Flower buds:

*Hardiness.*—Hardy, with respect to central California winters.

*Diameter.*—Typically 9⁄16" [14.3 mm.] 1 day before bloom.

*Length.*—Typically 15⁄16" [23.8 mm.] 1 day before bloom.

*Form.*—Not appressed.

*Surface.*—Pubescent.

*Color.*—Strong purplish red [255. s.pR] when tip is first exposed, Light purplish pink [249. l.pPk] just before bloom.

Flowers: Perfect, complete, perigynous, usually a single pistil, typically thirty or more stamens, five sepals and petal locations alternately positioned.

*Type.*—Showy, large.

*Average flower diameter.*—1 13⁄16" [46.0 mm.].

*Number of petals.*—Mostly five, but about ten percent are double blossoms and many possess extra smaller petals.

*Petal shape.*—Circular.

*Petal margin.*—Somewhat wavy.

*Average petal diameter.*—¾" [19.1 mm.].

*Average petal length.*—13⁄16" [20.6 mm.].

*Petal apex.*—Rounded with a small notch located at the top center of the margin on many.

*Petal base.*—Rounded.

*Petal color.*—Light purplish pink [249. l.pPk].

*Anther color.*—Dark red [16. d.R] over a Brilliant orange yellow [67. brill.OY] center.

*Stigma color.*—Light greenish yellow [101. l.gY].

*Sepal color.*—Dark purplish red [259. d.pR].

*Sepal length.*—¼" [6.4 mm.].

*Sepal width.*—11⁄64" [4.4 mm.].

*Average pistil length.*—¾" [19.1 mm.].

*Average stamen length.*—⅝" [15.9 mm.].

*Fragrance.*—Moderate when nectar is present.

*Blooming period.*—Medium compared with other varieties.

*Onset of bloom.*—One percent on Mar. 3, 2003.

*Date of full bloom.*—Mar. 10, 2003.

*Duration of bloom.*—One to two weeks, dependent on ambient temperature.

*Number per cluster.*—1 to 3 with single flowers most common.

FRUIT

Maturity when described: Firm ripe, Jun. 25, 2003.

Date of first picking: Jun. 21, 2003.

Date of last picking: Jun. 30, 2003.

Size: Uniform, large.

*Average diameter axially.*—2 9/16" [65.1 mm.].
*Average diameter across suture plane.*—2 5/8" [66.7 mm.].
*Typical weight.*—6.8 ounces [193 grams].
Form: Uniform, globose.
*Longitudinal section form.*—Circular.
*Transverse section through diameter.*—Circular.
Suture: A visible groove extending from the base well beyond the apex, sharp near the base, shallow along the side, and deep and somewhat sharp toward the apex.
Ventral surface: Rounded, lipped throughout on both sides.
Lips: Somewhat unequal.
Cavity: Flaring, elongated in the suture plane, suture showing on one side, and Greenish white [153. gWhite] stem markings typical.
*Depth.*—7/16" [11.1 mm.].
*Breadth.*—7/8" [22.2 mm.].
Base: Truncate.
Apex: Rounded and somewhat emarginate if viewed along the suture.
Pistil point: Some oblique and some apical, negligible in length, depressed within the suture.
Stem: Medium.
*Average length.*—3/8" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Nonastringent.
*Tendency to crack.*—None observed in dry season.
*Color.*—Very dark red [17. v.d.R] over a Moderate red [15. m.R] background with a minor amount of Light yellowish brown [76. l.yBr] freckling toward the apex and some very small Light yellow green [119. l.YG] areas in the stem cavity where sunlight deprived.
Flesh:
*Color.*—White [263. White] to Greenish white [153. gWhite] toward the stone with occasional Moderate red [15. m.R] flecking toward the skin when reaching past maturity.
*Surface of pit cavity.*—Greenish white [153. gWhite] fibers breaking when twisted from the stone.
*Amygdalin.*—Scarce.
*Juice.*—Abundant, rich.
*Texture.*—Firm and very crisp.
*Fibers.*—Abundant, fine.
*Ripens.*—Slightly earlier toward the apex.
*Flavor.*—Mildly sub-acidic and sweet, averaging 17 brix.
*Aroma.*—Slight.
*Eating quality.*—Very good.

STONE

Type: Clingstone.
Form: Oval.
Hilum: Oval.
Base: Fairly straight.
Apex: Rounded to cuneate with a slightly protruding tip and an average tip angle of 90 degrees.
Sides: Equal.
Surface: Irregularly furrowed near the apex and pitted toward the base.
Ridges: Jagged toward the base.
External color: Light orange [52. l.O] when freshly exposed.
Pit wall color when cracked: Pale orange yellow [73. p.OY].
Internal cavity color: Light yellowish brown [76. l.yBr].
Average pit wall thickness: 1/4" [6.4 mm.].
Average width: 1 1/16" [27.0 mm.].
Average length: 1 9/16" [39.7 mm.].
Average breadth: 13/16" [20.6 mm.].
Tendency to split: Slight.
Kernel:
*Form.*—Oval.
*Pellicle color.*—Light grayish yellowish brown [79. l.gy.yBr].
*Skin color.*—Pale yellow [89. p.Y] when first cracked.
*Vein color.*—Pale orange yellow [73. p.OY].
*Taste.*—Bitter.
*Viable.*—Yes.
*Average width.*—1/2" [12.7 mm.].
*Average length.*—13/16" [20.6 mm.].
*Amygdalin.*—Abundant.

USE

Market: Fresh market and long distance shipping.
Keeping quality: Good. Fruit quality observed to remain in good condition in after 14 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'June Pearl' (U.S. Plant Pat. No. 9,360) nectarine, by producing nectarines that are very firm in texture, sub-acidic and sweet in flavor, clingstone in type, and nearly full red in skin color, but is distinguished therefrom by producing fruit that is more globose in shape, has virtually no protruding tips at the apex, is larger in size, and matures about five days later.

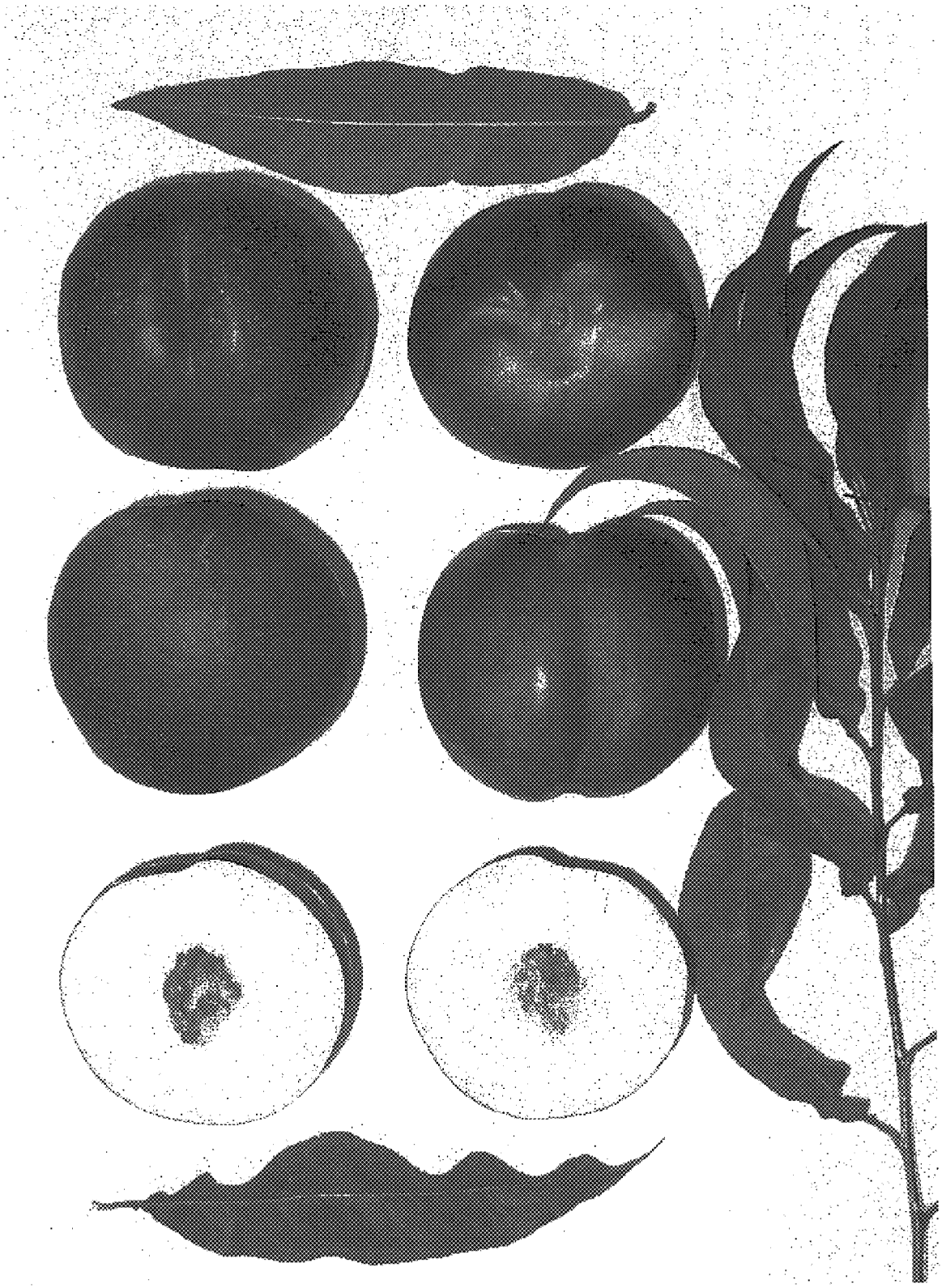

* * * * *